United States Patent [19]

Medero et al.

[11] Patent Number: 5,800,359
[45] Date of Patent: Sep. 1, 1998

[54] NIBP PLAYBACK SYSTEM

[75] Inventors: Richard Medero; John W. Booth, both of Tampa, Fla.

[73] Assignee: Johnson & Johnson Medical, Inc., New Brunswick, N.J.

[21] Appl. No.: 445,273

[22] Filed: May 19, 1995

[51] Int. Cl.⁶ .................................................. A61B 5/02
[52] U.S. Cl. ...................... 600/454; 73/4 R; 600/493
[58] Field of Search .............................. 128/681–687, 128/672–675, 748; 73/4 R

[56] References Cited

U.S. PATENT DOCUMENTS

| | | | |
|---|---|---|---|
| 4,349,034 | 9/1982 | Ramsey, III | 128/681 |
| 4,360,029 | 11/1982 | Ramsey, III | 128/681 |
| 4,461,266 | 7/1984 | Hood, Jr. et al. | 128/681 |
| 4,464,123 | 8/1984 | Glover et al. | 434/268 |
| 4,543,962 | 10/1985 | Medero et al. | 128/682 |
| 4,546,775 | 10/1985 | Medero | 128/681 |
| 4,627,440 | 12/1986 | Ramsey, III et al. | 128/682 |
| 4,638,810 | 1/1987 | Ramsey, III et al. | 128/681 |
| 4,754,761 | 7/1988 | Ramsey, III et al. | 128/683 |
| 4,774,960 | 10/1988 | Arnold et al. | 128/681 |
| 4,799,492 | 1/1989 | Nelson | 128/672 |
| 4,889,133 | 12/1989 | Nelson et al. | 128/681 |
| 4,926,873 | 5/1990 | Frankenreiter | 128/681 |
| 4,949,710 | 8/1990 | Dorsett et al. | 128/680 |
| 4,953,557 | 9/1990 | Frankenreiter et al. | 128/677 |
| 4,984,577 | 1/1991 | Frankenreiter | 128/681 |
| 5,016,466 | 5/1991 | Ness et al. | 73/4 R X |
| 5,027,641 | 7/1991 | Costello, Jr. | 73/4 R X |
| 5,052,397 | 10/1991 | Ramsey, III et al. | 128/682 |
| 5,054,495 | 10/1991 | Uemura et al. | 128/680 |
| 5,103,833 | 4/1992 | Apple | 128/687 |
| 5,170,795 | 12/1992 | Ramsey, III et al. | 128/682 |
| 5,218,968 | 6/1993 | Apple | 128/687 |
| 5,253,648 | 10/1993 | Walloch | 128/681 |
| 5,261,413 | 11/1993 | Kawahara | 128/682 |
| 5,280,790 | 1/1994 | Brooks | 128/681 |
| 5,311,872 | 5/1994 | Apple | 128/687 |
| 5,505,206 | 4/1996 | Walloch | 128/681 |

FOREIGN PATENT DOCUMENTS 0642740  3/1995  European Pat. Off. .

*Primary Examiner*—Robert L. Nasser
*Assistant Examiner*—Ryan Carter
*Attorney, Agent, or Firm*—Woodcock Washburn Kurtz Mackiewicz & Norris LLP

[57] ABSTRACT

A data playback device which records, stores, and plays back actual patient oscillometric blood pressure data to create a more realistic NIBP simulation for testing of an NIBP monitor. The system is made up of two units, a computer and a converter. The converter has a Universal Asynchronous Receiver/Transmitter (UART) connected to the computer and 16-bit D/A and A/D converters connected to the input and output, respectively, of a blood pressure monitor. The A/D converter senses cuff pressure and sends the signal to the computer. The computer then calculates the pressure pulse data from the stored patient data and sends it to the monitor via the D/A converter, where the pressure pulse data is converted to a voltage and electronically summed with the pressure transducer signal output by the blood pressure monitor under test. Typically, the playback system reads the current cuff pressure in the blood pressure monitor and "plays back" the oscillation complex from the data file whose average pressure is closest to the current cuff pressure. The oscillation complex is scaled to the proper amplitude using linear interpolation before it is summed into the cuff pressure channel. This process is repeated for each pressure level during the oscillometric blood pressure determination. During testing, the blood pressure monitor sees an oscillation envelope and oscillation complex shapes similar to the original data from a real patient.

33 Claims, 7 Drawing Sheets

NIBP PLAYBACK SYSTEM

FIELD OF THE INVENTION

This invention relates to automated blood pressure monitoring using the oscillometric method and, more particularly, to automated devices for simulating the presence of patients to oscillometric blood pressure monitors.

BACKGROUND OF THE INVENTION

The sphygmomanometric class of automated blood pressure monitors employs an inflatable cuff to exert controlled counter-pressure on the vasculature of a patient. One large class of such monitors, exemplified by that described in U.S. Pat. Nos. 4,349,034 and 4,360,029, both to Maynard Ramsey, III and commonly assigned herewith and incorporated by reference, employs the oscillometric methodology. In accordance with the Ramsey patents, an inflatable cuff is suitably located on the limb of a patient and is pumped up to a predetermined pressure above the systolic pressure. Then, the cuff pressure is reduced in predetermined decrements, and at each level, arterial pressure fluctuations caused by the heart contractions are monitored. As the arterial pressure increases as a result of the heart contraction, the circumference of the arteries increases due to the elasticity of the arterial walls. The peak of the resultant arterial pressure is known as the systolic pressure. As the heart relaxes between beats, the arterial walls return to their normal size and the arterial pressure returns to a minimum pressure known as the diastolic pressure. One complete cycle of the arterial pressure increasing with the heart contraction and then returning to its relaxed pressure state as the heart relaxes is known as a blood pressure "oscillation" or "oscillation complex".

Thus, as the cuff pressure is decremented from some point above systolic, the blood pressure oscillation complexes will increase in amplitude to a maximum height at a cuff pressure known as the mean arterial pressure ("MAP"). MAP represents an average of the systolic and diastolic levels. The oscillation complexes now decrease in amplitude as the cuff pressure is further reduced. The general shape of the amplitude peaks of the oscillation complexes as the cuff pressure is lowered from above systolic to below diastolic is known as the oscillometric envelope.

The measured arterial pulse signals typically consist of a DC voltage with a small superimposed variational component caused by the arterial blood pressure pulsations. The oscillation complexes typically have amplitudes which are about one percent that of the arterial pulse signals. After suitable filtering to reject the DC component and to provide amplification by a scale factor, peak amplitudes of the oscillations above a given base-line are measured and stored. As the decrementing continues, the peak amplitudes will normally increase from a lower level to a relative maximum, and thereafter will decrease to form the afore-mentioned oscillometric envelope for the patient. The lowest cuff pressure at which the oscillations have a maximum value is representative of the MAP of the patient. The systolic and diastolic pressures can be derived either as predetermined fractions of the oscillation size at MAP, or by more sophisticated methods of direct processing of the oscillation complexes or oscillometric envelope.

The step deflation technique as set forth in the Ramsey patents is the commercial standard of operation. A large percentage of clinically acceptable automated blood pressure monitors utilize the step deflation rationale. When in use, the blood pressure cuff is placed on the patient and the operator usually sets a time interval, typically from 1 to 90 minutes, at which blood pressure measurements are to be made. The noninvasive blood pressure ("NIBP") monitor automatically starts a blood pressure determination at the end of the set time interval.

FIG. 1 illustrates a simplified version of the oscillometric blood pressure monitor described in the aforementioned Ramsey patents. In FIG. 1, the arm 100 of a human subject is shown wearing a conventional flexible inflatable and deflatable cuff 101 for occluding the brachial artery when inflated. As the cuff 101 is deflated using deflate valve 102 having exhaust 103, the arterial occlusion is gradually relieved. The deflation of cuff 101 via deflate valve 102 is controlled by microprocessor 107 via control line 108.

A pressure transducer 104 is coupled by a duct 105 to the cuff 101 for sensing the pressure therein. In accordance with conventional oscillometric techniques, pressure oscillations in the artery are sensed by changes in the counter-pressure of the cuff 101, and these pressure oscillations are converted into an electrical signal by transducer 104 and coupled over path 106 to microprocessor 107 for processing. In addition, a source of pressurized air 109 is connected via a duct 110 through an inflate valve 111 and a duct 112 to the pressure cuff 101. The inflate valve 111 is electrically controlled through a connection 113 from the microprocessor 107. Also, the deflate valve 102 is connected by duct 114 via a branch connection 115 with the duct 112 leading to cuff 101.

During operation of the apparatus illustrated in FIG. 1, air under pressure to about 8–10 p.s.i. is typically available in the source of pressurized air 109. When it is desired to initiate a determination of blood pressure, the microprocessor 107 furnishes a signal over path 113 to open the inflate valve 111. The deflate valve 102 is closed. Air from the source 109 is communicated through inflate valve 111 and duct 112 to inflate the cuff 101 to a desired level, preferably above the estimated systolic pressure of the patient. Microprocessor 107 responds to a signal on path 106 from the pressure transducer 104, which is indicative of the instantaneous pressure in the cuff 101, to interrupt the inflation of the cuff 101 when the pressure in the cuff 101 reaches a predetermined value above the estimated systolic pressure of the patient. Such interruption is accomplished by sending a signal over path 113 instructing inflate valve 111 to close. Once inflate valve 111 has been closed, the blood pressure measurement can be obtained by commencing a step deflate or a continuous deflate routine.

Microprocessor 107 processes the signals from pressure transducer 104 to produce blood pressure data and to reject artifact data as described in the afore-mentioned Ramsey '029 and '034 patents. The blood pressure may be determined in accordance with the teachings of Medero et al. in U.S. Pat. No. 4,543,962, of Medero in U.S. Pat. No. 4,546,775, of Hood, Jr. et al. in U.S. Pat. No. 4,461,266, of Ramsey, III et al. in U.S. Pat. No. 4,638,810, of Ramsey, III et al. in U.S. Pat. No. 4,754,761, of Ramsey, III et al. in U.S. Pat. No. 5,170,795, and of Ramsey, III et al. in U.S. Pat. No. 5,052,397, all of which are commonly assigned herewith and the disclosures of which are hereby incorporated by reference. Any of these known techniques are used to determine the quality of the oscillation complexes received at each level so that the blood pressure determination is made using actual blood pressure data and not artifact data.

Actual measurement of the blood pressure under the control of the microprocessor 107 and the deflate valve 102 and as sensed by pressure transducer 104 can be accomplished in any suitable manner such as that disclosed in the aforementioned patents. At the completion of each measurement cycle, the deflate valve 102 can be re-opened long enough to relax the cuff pressure via exhaust 103. Thereafter, the deflate valve 102 is closed for the start of a new measurement cycle.

Accordingly, when a blood pressure measurement is desired, the inflate valve 111 is opened while the cuff pressure is supervised by pressure transducer 104 until the cuff pressure reaches the desired level. The inflate valve 111 is then closed. Thereafter, the deflate valve 102 is operated using signal 108 from microprocessor 107 and the blood pressure measurement taken.

Prior art FIG. 2 illustrates a pressure versus time graph of the raw data resulting from a conventional cuff step deflation and measurement cycle for a conventional NIBP monitor. As illustrated, the cuff 101 is inflated to a pressure above the systolic pressure, and the cuff 101 is then step deflated to the next pressure level. A timeout duration d is provided at each step during which the signal processing circuitry searches for oscillation complexes in accordance with the techniques described in the afore-mentioned commonly assigned patents. At the end of timeout duration d, the cuff pressure is decremented even if no oscillation complex is detected. This process of decrementing the pressure and searching for oscillation complexes is repeated at least until MAP, the oscillometric envelope 200 may be calculated, and/or the pressure drops below a predetermined level. The entire blood pressure determination process is then repeated at intervals set by the user, some other predetermined interval, or manually.

As shown in FIG. 2, the patient's arterial blood pressure data forms an oscillometric envelope 200 comprised of a set of oscillation amplitudes measured at the different cuff pressures. From oscillometric envelope 200, systolic, MAP and diastolic blood pressures are typically calculated. As noted in the afore-mentioned patents, it is desired that all artifact data be rejected from the measured data so that oscillometric envelope 200 contains only the desired amplitude data and no artifacts, thereby improving the accuracy of the blood pressure determinations. Generally, conventional NIBP monitors of the type described in the afore-mentioned patents use oscillation amplitude matching at each pressure level as one of the ways to discriminate good oscillations from artifacts. In particular, pairs of oscillations are compared at each pressure level to determine if they are similar in amplitude and similar in other attributes, such as shape, area under the oscillation curve, slope, and the like. If the oscillations compare within predetermined limits, the average amplitude and cuff pressure are stored and the pressure cuff is deflated to the next pressure level for another oscillation measurement. However, if the oscillations do not compare favorably, the monitor does not deflate; instead, the monitor waits for another oscillation to compare with one or more of the previous oscillations. This process continues until two oscillations match or a time limit is exceeded.

The testing of such automatic blood pressure monitors is typically very difficult because living test subjects may have different pressure levels at different times, and different subjects have different blood pressure levels. As a result, simulated arms have been developed which simulate the arm of a living subject to be tested for blood pressure readings by the oscillometric method. For example, Glover et al. describe in U.S. Pat. No. 4,464,123, which is assigned to the present assignee and incorporated herein by reference, an arm simulator or monitor calibrator which automatically induces pressure pulses in the cuff of an oscillometric blood pressure monitor at predetermined, selectable rates and having amplitudes at preprogrammed cuff pressures that indicate a user selected value for systolic, diastolic, MAP, and pulse rate. The arm simulator described by Glover et al. includes a pressure chamber with an electrically actuated diaphragm adapted to generate pressure pulses related to an applied electrical signal. The pressure pulses are added to the pressure from the cuff to simulate the oscillation complexes. The signal which drives the diaphragm typically has a repetition rate that represents a selected pulse rate and an amplitude that varies with the applied pressure in the cuff so as to simulate the pressure pulsations of a patient with selected diastolic, systolic, and MAP values. The amplitudes of the pressure pulses and the rate are calculated and controlled by a microprocessor in response to the selected pulse rate and pressure values. Unfortunately, such simulators are limited by the diaphragm in their dynamic response, range and resolution of the pressure pulse generator.

Accordingly, an improved simulator is desired which has a wide dynamic range and high resolution.

An improved simulator is also desired which allows for simulation or playback of real patient cuff pressure data without using a mechanical diaphragm or the like.

SUMMARY OF THE INVENTION

A device and a method are described which meet the above-mentioned needs in the art by providing an electrical simulation signal directly to the monitor's pressure transducer circuit. The inventors have found that this allows a much more accurate simulation signal to be sensed by the unit under test (UUT), which permits a more accurate simulation. In accordance with the invention, the electrical simulation signal may further include real patient cuff pressure data which is played back to create a more realistic NIBP simulation.

The simulation system described herein is used for testing NIBP monitors and algorithms. The system can simulate NIBP signals by using a math model for envelope and pulse shapes, or, as just noted, it can use real cuff pressure signals that were recorded during actual NIBP determinations on patients as the simulation data.

The system is made up of two units, a computer and a converter. The converter has a Universal Asynchronous Receiver/Transmitter (UART) connected to the computer and 16-bit D/A and A/D converters connected to the input and output, respectively, of a blood pressure monitor. The A/D converter senses cuff pressure and sends the signal to the computer. The computer then calculates the pressure pulse data from the stored patient data and sends it to the UUT via the D/A converter, where the pressure pulse data is converted to a voltage and added to the cuff pressure transducer signal output by the UUT. This process is repeated for each pressure level during the oscillometric blood pressure determination.

Since the raw cuff pressure data from the patient includes a set of pressure levels (DC) and pressure pulse data (AC), the raw cuff pressure data is processed by the computer before being sent to the UUT. In particular, the cuff effect is removed by rotating the data representing a pressure pulse so that the end points of the data are at the same level. The DC pressure component is also removed. The raw cuff pressure data is further scaled and time adjusted as necessary. During playback, the system senses the cuff pressure generated by the UUT, selects the patient data closest to the cuff pressure level, and sends the patient data to the D/A converter connected to the UUT, where the data is added to the cuff pressure signal. The patient data stored for that pressure level are repeated until the UUT changes cuff pressure to a new pressure level. The process is then repeated for the stored patient data at the pressure level nearest to the new pressure level until a patient envelope is created.

The simulation or playback system of the invention collects raw data in a clinical environment by digitizing the cuff pressure waveform during an NIBP determination. The digitized waveform is then converted into a playback data file by extracting actual oscillation complexes, their amplitudes, and the cuff pressure for each. Extracting this data preserves the shape and amplitude of the original oscillation complexes. Calibration information is also saved with each file to correlate the raw waveforms to pressure.

During operation, a blood pressure monitor to be tested is connected to a cuff wrapped around a cylinder to keep the volume in the cuff equivalent to the volume during the original determination. The blood pressure monitor controls the pressure in the cuff at all times. The simulation or playback system of the invention then electronically sums the oscillation complexes into the cuff pressure waveform when the pressure is within the pressure range of the digitized and stored data. The simulation or playback system reads the current cuff pressure in the blood pressure monitor and "plays back" the oscillation complex from the data file whose average pressure is closest to the current cuff pressure. The oscillation complex is scaled to the proper amplitude using linear interpolation before it is summed into the cuff pressure channel.

The method of the invention results in blood pressure monitor seeing an oscillation envelope and oscillation complex shapes similar to the original data from a real patient. The blood pressure monitor interprets this information for corresponding blood pressure parameters throughout the dynamic range of the monitor.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PRESENTLY PREFERRED EMBODIMENT

A system and method which meets the above-mentioned objects and provides other beneficial features in accordance with the presently preferred exemplary embodiment of the invention will be described below with reference to FIGS. 3-7. Those skilled in the art will readily appreciate that the description given herein with respect to those figures is for explanatory purposes only and is not intended in any way to limit the scope of the invention. Also, common reference numbers are used throughout the drawings to represent common elements. All questions regarding the scope of the invention should be resolved by referring to the appended claims.

Figure 1:
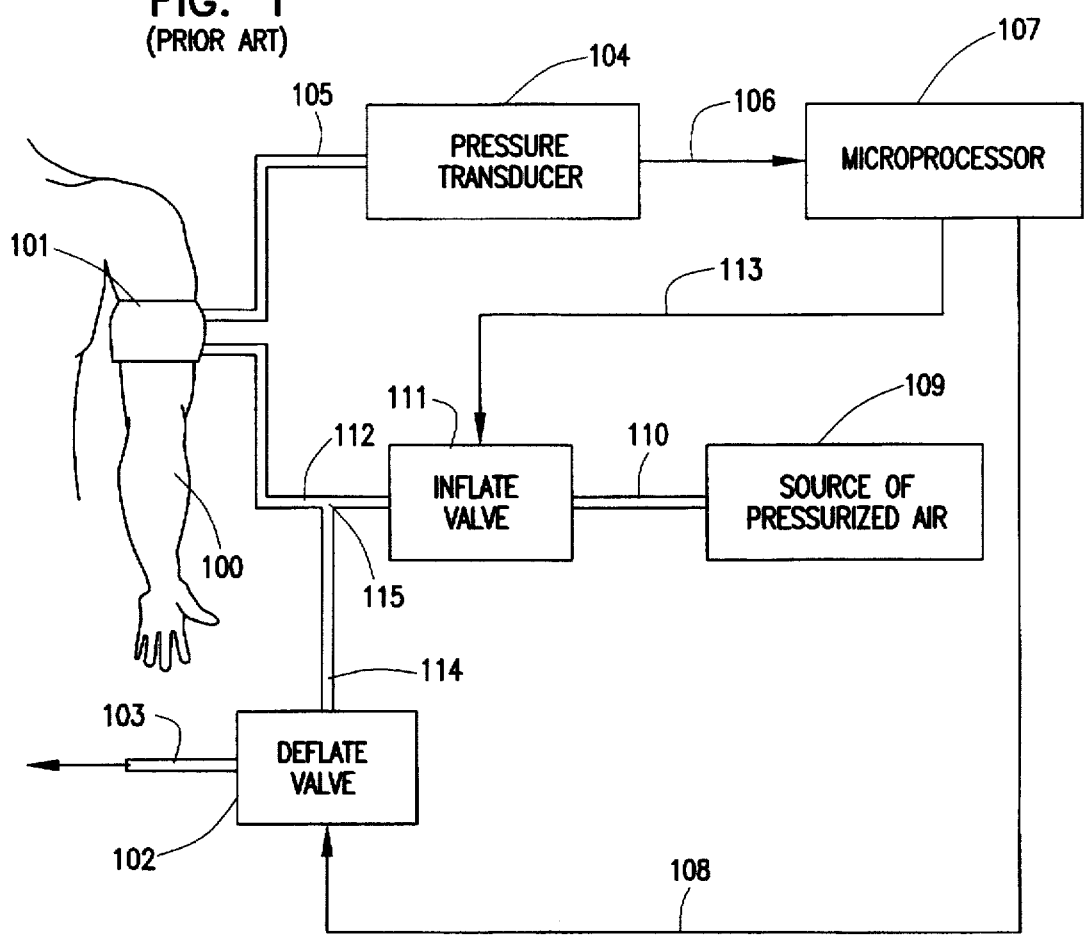
FIG. 1 is a schematic representation of a conventional noninvasive blood pressure ("NIBP") monitor of the type tested by the present invention.
Figure 2:
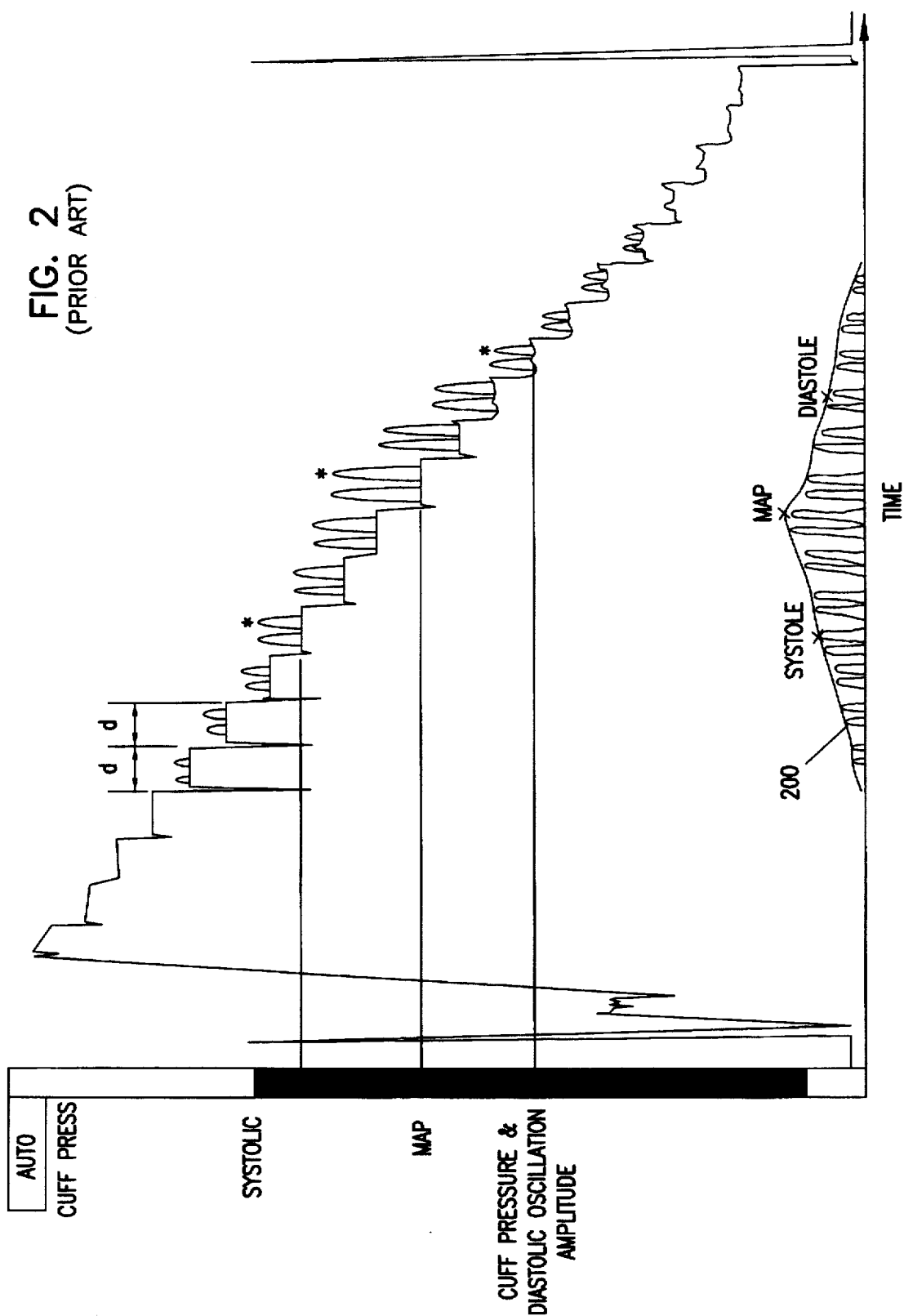
FIG. 2 is a pressure versus time graph illustrating a measuring cycle including deflation steps and the corresponding oscillation complexes measured using the conventional NIBP monitor of FIG. 1.
Figure 3:
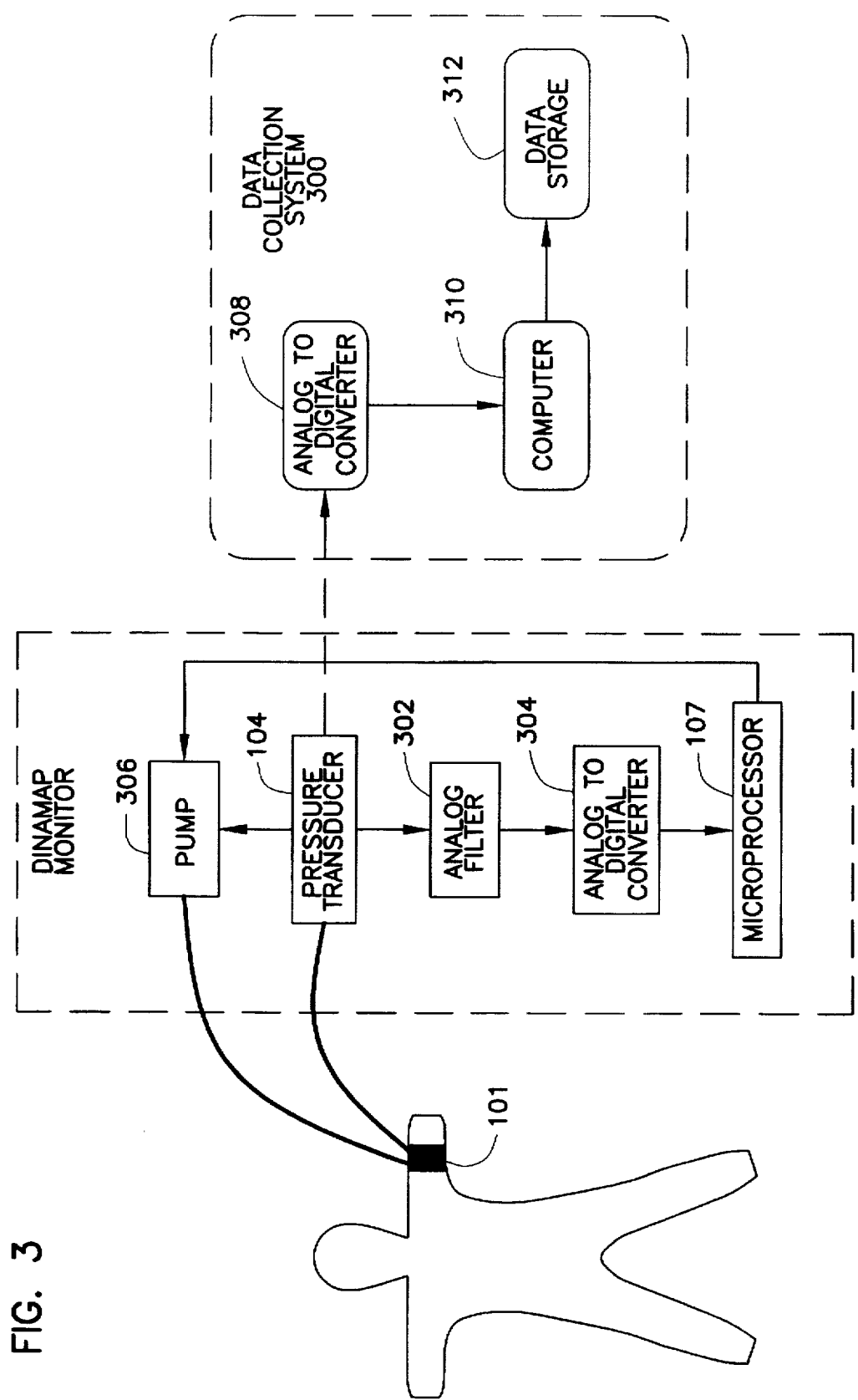
FIG. 3 is a block diagram of a patient oscillometric blood pressure data collection system in accordance with the invention.

FIG. 3 illustrates a data collection system 300 for collecting the raw patient oscillometric blood pressure data of the type illustrated in FIG. 2. As illustrated, a pressure cuff 101 is placed on a patient, and the patient's blood pressure is monitored using an oscillometric blood pressure monitor such as the DINAMAP™ Monitor available from Johnson & Johnson Medical, Inc. As illustrated, the DINAMAP™ Monitor includes a pressure transducer 104 for measuring the pressure within pressure cuff 101, an analog filter 302 for removing the DC blood pressure data from the composite blood pressure data from the pressure transducer 104, an A/D converter 304 for converting the remaining oscillometric complex data from the A/D converter 302 and the DC blood pressure data provided directly from the pressure transducer 104 to digital form, an inflate/deflate air pump 306 for controlling the pressure of pressure cuff 101, and a microprocessor 107 which controls inflate/deflate air pump 306 to carry out the step inflate/deflate routine. As illustrated, the data collection system 300 of the invention is connected to the output of the pressure transducer 104 for collecting and storing the raw data output by the pressure transducer 104 during an oscillometric blood pressure measurement of the patient.

In a preferred embodiment, data collection system 300 comprises a high resolution (preferably 16-bit) A/D converter 308 driven by a state machine. A UART (FIG. 6) provides two way communications between the A/D converter 308 and the computer 310, which may be, for example, a MACINTOSH™ computer available from Apple Corporation. Applications software of computer 310 formats the raw data from the pressure transducer 104 into binary data files for storage in data storage device 312. The control software for data collection may be, for example, an application program used in conjunction with analog to digital converter 308 for digitizing and storing the analog waveforms in a binary format. In a preferred embodiment, the application program used for this purpose, as well as the associated hardware, can be configured to digitize up to eight analog channels at a maximum sampling rate of 960/(number of channels) samples per second. The collected raw data can then be used as input data for the development of physiological parameter measurement devices in accordance with the invention. In addition, it is preferred that calibration information which allows translation of the A/D units into pressure be stored with the binary files.

As just noted, the data files stored in raw data storage 312 are the raw cuff pressure waveforms and are formatted so as to facilitate extraction of pertinent waveform data. In a preferred embodiment, the waveform data is extracted from the raw data in raw data storage 312 using an application program of computer 310. Such an application program is very similar to that used to collect the raw data except that the raw data files are read and displayed to the user. Post processing such as filtering or waveform analysis also may be performed on the raw signals. Data segments of interest may be selected, zoomed, and/or output to a text file along with the calibration information.

Figure 4:
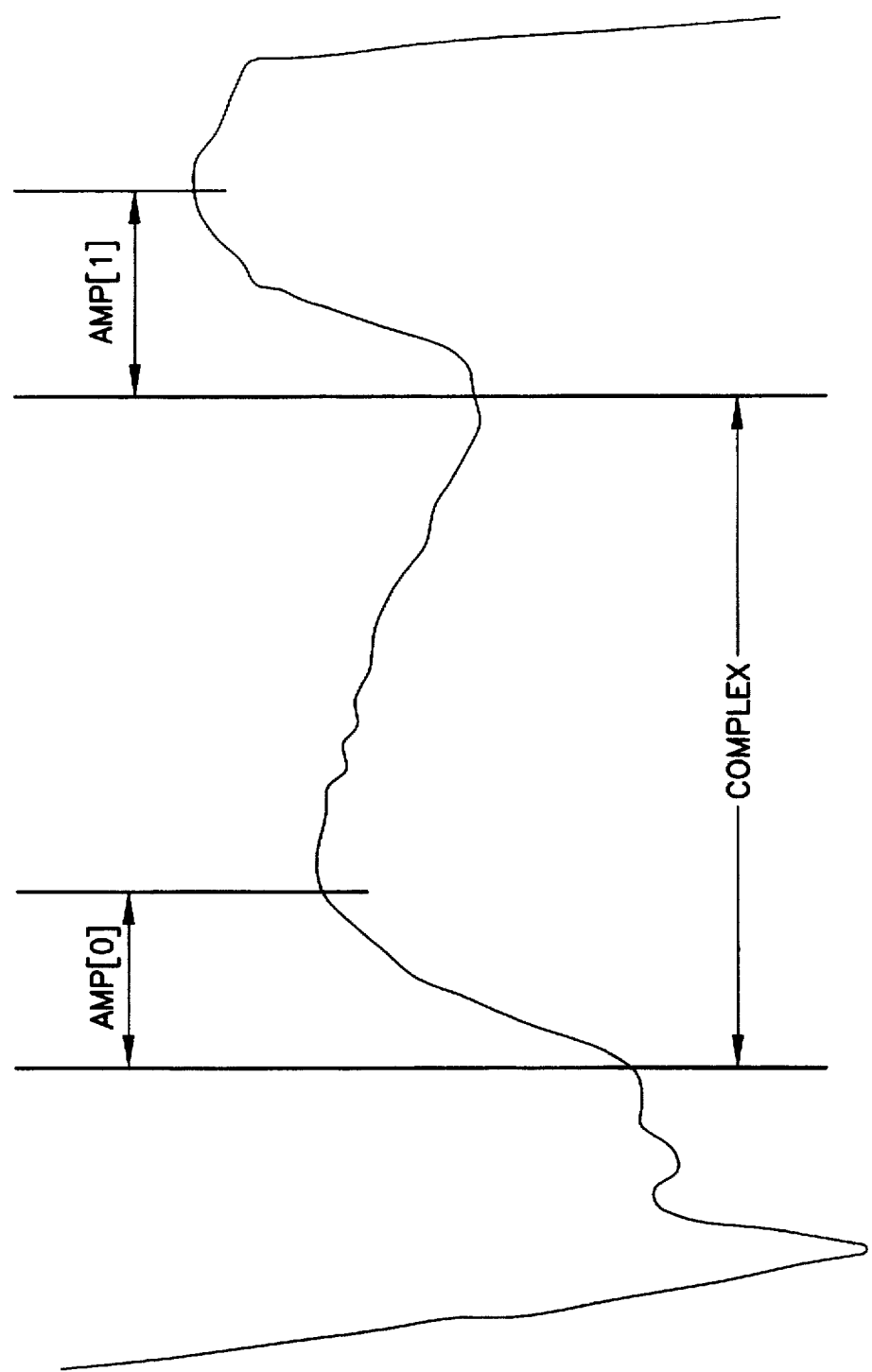
FIG. 4 illustrates a portion of a single step of the raw data file shown in FIG. 2.

The extraction of pertinent data from a raw data file begins by selecting and outputting a one second interval to a text file as a record to let a data playback program of computer 310 know the sampling rate of the raw data. Portions of the raw data file are then selected. FIG. 4 represents one step of the selected raw data file shown in FIG. 2. The raw oscillometric data between the beginning of an oscillation complex and its peak is appended to the text file as another record. As shown in FIG. 4, two amplitudes (Amp[0] and Amp[1]) are preferably selected and stored in separate records. If there are more than two oscillation complexes at the raw data's step, the last two are used because these are the oscillation complexes the monitor selected before deflating/inflating to the next pressure level. These records represent the amplitude of the oscillation complex. The average of the two records is used for interpolating the amplitude of the data during play back of the stored oscillometric data.

Next, the raw data for an entire oscillation complex is appended to the text file as another record. The oscillation complex is selected to cover the time period from the beginning of one cycle of the oscillation complex to the beginning of the next oscillation complex. Preferably, one of the oscillation complexes that the original monitor selected is used for this purpose. Those skilled in the art will appreciate that more than one oscillation complex can be stored for a deflation step; however, they must be continuous.

The process of selecting two amplitudes and then a full oscillation complex is repeated for every deflation step in the raw data file that has detectable oscillation complexes. Additionally, the text files may be converted to binary format using, for example, a Macintosh Programmers Workshop (MPW) tool. This is done to increase the speed of reading the stored data files. As will be described below, the resulting records form the data files which are played back during a simulation.

In summary, the stored waveform data forming the playback files has the following format:

The first line in the file has the calibration data. For example: 6147 A/D units @ 0 mm Hg; 45733 A/D units @ 171 mm Hg. The calibration information is repeated between each record.

A first record has one second of data which is used to determine the rate that the data was collected.

The following three records are then stored for each pressure step in the raw data:

The first of the three records has the amplitude of the first oscillation complex.

The second of the three records has the amplitude of the second oscillation complex.

The third of the three records has the entirety of the oscillation complex data.

The remaining records repeat these three records for each of the pressure steps.

Figure 5:
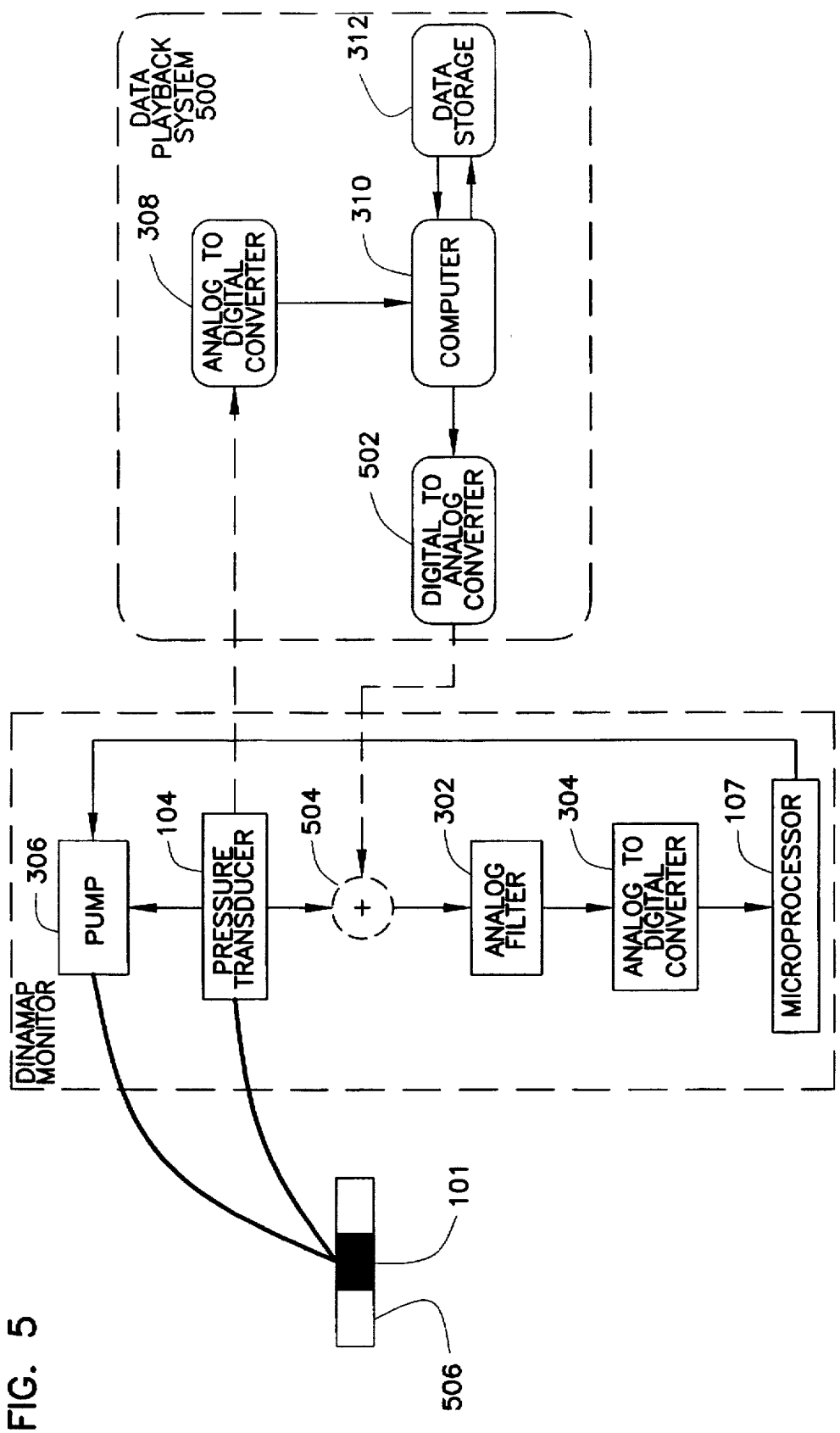
FIG. 5 is a block diagram of an oscillometric blood pressure simulation data playback system in accordance with the invention.

FIG. 5 illustrates an oscillometric blood pressure simulation data playback system 500 in accordance with the invention. As illustrated, data playback system 500 is substantially the same as that shown in FIG. 3 except that computer 310 reads out data stored in playback storage 501 and converts the output data to analog form using D/A converter 502 for addition at adder 504 to the electrical signal representing the DC pressure output of pressure transducer 104 when cuff 101 is placed around a constant diameter cylinder 506. Further details regarding the data playback (patient simulation) system in accordance with the invention will be provided below with reference to FIGS. 6 and 7.

Figure 6:
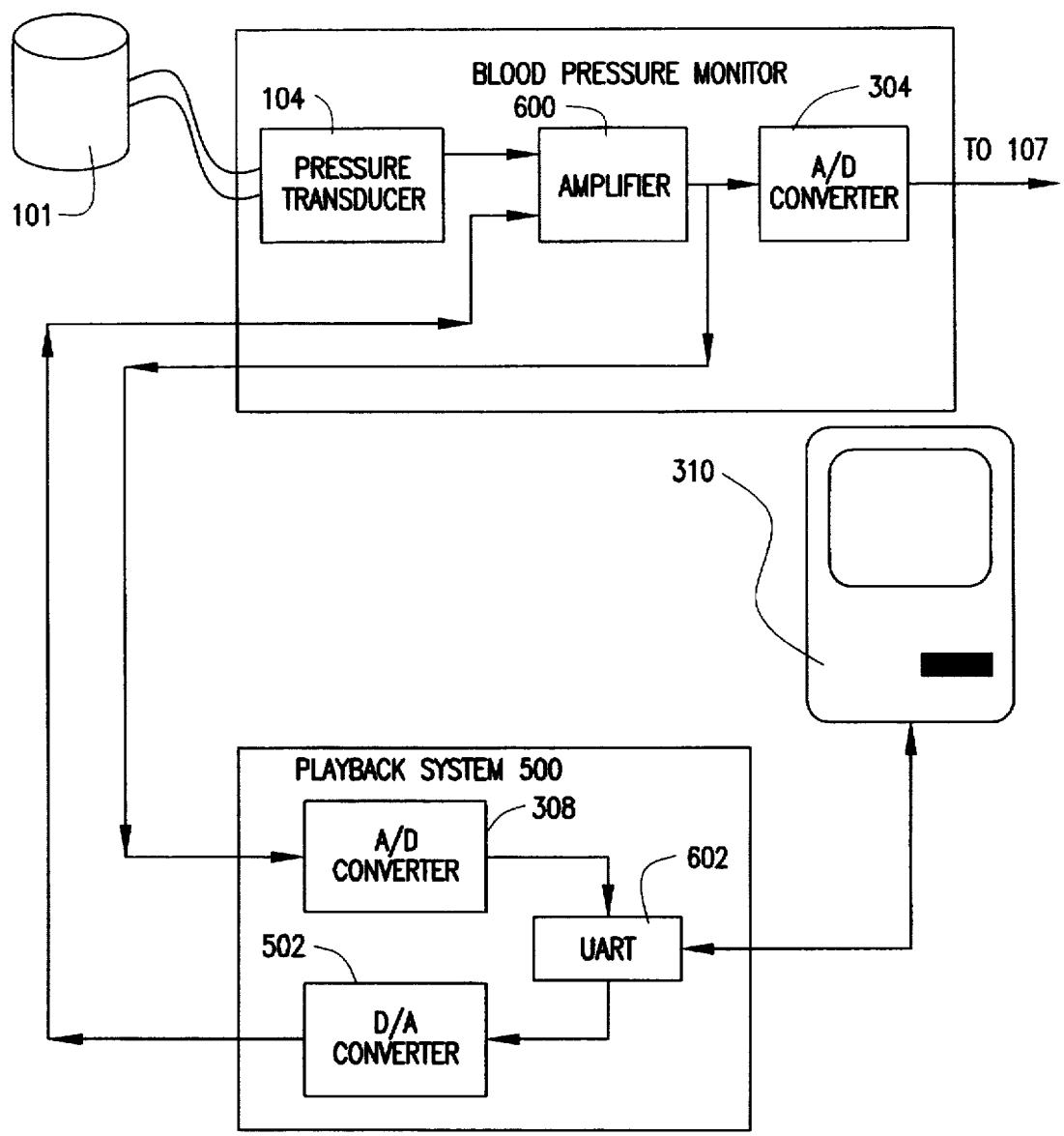
FIG. 6 illustrates the playback system hardware in accordance with a preferred embodiment of the invention.

FIG. 6 illustrates the system hardware for data playback system 500. As illustrated, data playback system 500 uses a 16-bit A/D converter 308 to monitor the cuff pressure output by amplifier 600. The cuff pressure is then sent to computer 310 via UART 602. Computer 310 reads the cuff pressure, identifies the data closest to the cuff pressure, and then scales the data as appropriate. The data is then sent from computer 310 to D/A converter 502 via UART 602 and then summed into the output of pressure transducer 104 by transducer amplifier 600.

When a NIBP monitor is to be tested, an appropriate data file is read in from playback memory 501 for use in the simulation. While reading the data file into processor memory, the calibration numbers of the UUT are used along with the calibration numbers in the data file to convert the data to the scaling of the UUT. After conversion to the scaling of the UUT, the average pressure of each oscillation complex is stored in processor memory.

Figure 7A:
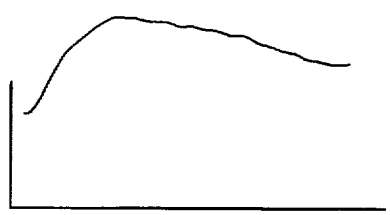
FIG. 7(a) illustrates an oscillation complex taken from the raw data shown in FIG. 4.
Figure 7B:
FIG. 7(b) illustrates the oscillation complex of FIG. 7(a) after correction for the cuff effect.

The data stored in the processor memory is processed before being used in the simulation. For example, since the end points of a raw oscillation complex are not equal (FIG. 7(a)), there would be a discontinuity when the oscillation complex is played back repeatedly. To eliminate this, the data is rotated until the end points are at the same level as shown in FIG. 7(b). This removes the so-called "air effect", which is a change in pressure due to thermal changes, and the so-called "cuff effect", which is defined as the effects due to the elasticity properties of the pressure cuff.

In addition, since the raw data may have been collected at rates of 960 samples per second using from 1 to 8 data channels, the rate of data collection varies depending on the number of channels used and the speed selected when the data was collected. By contrast, a preferred embodiment of the data playback system 500 outputs data at a rate of 240 samples per second. If the data was not collected at 240 samples per second, then the data must be adjusted to this rate. This is accomplished by interpolating or decimating samples between actual samples to achieve the desired rate of 240 samples per second.

Figure 7C:
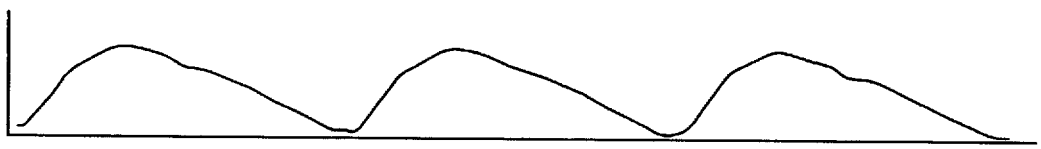
FIG. 7(c) illustrates the oscillation complex of FIG. 7(b) after removal of the DC pressure component.

The last step in the preparation of the data prior to feedback to the blood pressure monitor during a simulation is the removal of the DC component from the oscillation complex, as shown in FIG. 7(c). The minimum value is subtracted from all the samples.

The software processing characteristics of the playback system 500 are preferably stored in a Startup file. In other words, the Startup file contains parameters specifying what type of processing is to be performed on the stored waveform data. For example, in a preferred embodiment, the Startup file contains parameters which allow for randomly varying the amplitude and rate of the playback data, for adding noise to the playback data, for choosing an envelope mode in which a synthetic envelope is generated, and the like. Once the Startup file is read, the input file is read in from playback storage 501. The input file is then processed in accordance with the parameters specified in the Startup file.

For example, the input data may be interpolated during playback. Interpolation is desired since the measured oscillation complex amplitude values are dependent on cuff pressure. Since the cuff pressure of the unit under test (UUT) is rarely at the same pressure that the simulation data was collected, interpolation is used to calculate what the amplitude would have been during the original determination. The data is then scaled to that amplitude before being summed into the cuff signal by adder 504. When no data scaling is provided, the control process will pick the data that is closest to the current cuff pressure and then play the data back at its original amplitude instead of scaling the data before playback.

If the debug mode is selected, computer 310 prints out information about the processing of the input files from playback storage 501. This allows the simulation process to be monitored for errors.

The zero offset, in A/D units, of the UUT may also be determined. If an offset parameter greater than zero is passed by the Startup file, then zeroing is skipped. Otherwise, the operator is asked to either manually enter the zero value or to initiate an automatic read of the zero value. If an automatic read of the zero value is selected, the operator is asked to deflate the cuff 101. At this point, samples are taken and averaged to determine the zero offset.

A parameter may also be processed to determine the number of A/D units between the zero offset value and a predetermined pressure such as 200 mm Hg for the UUT. If a parameter value greater than zero is passed by the Startup file, then the span procedure is skipped. Otherwise, the operator is asked to either manually enter the span value or to initiate an automatic read of the span value. If an automatic read is selected, the operator is asked to inflate the cuff 101 to the predetermined pressure, e.g., 200 mm Hg. At this point, samples are taken and averaged to determine the span value.

Amplitude and rate variability are also selectable in the Startup file. Amplitude and rate variability permits the amplitude of the oscillations and/or the period of the oscillations to be randomly varied within limits set by the operator. These features help to approximate actual patient data that fluctuate over time.

The processing system may also allow the operator to sum an external noise file with the signal output by the pressure transducer 104. This feature may be used primarily as a developmental tool to compare one software revision to another. The noise data is summed into the oscillation complex data at a level equal to (n/100) times the noise data, where n represents the percentage of the noise file's amplitude. Generally, the noise file is collected and processed in the same way as the oscillation complex data. The format of the noise data file is preferably the same as the oscillation complex data files except that amplitude records are not used.

Finally, the NIBP playback system of the invention may use data collected on actual patients or it can create its own data. When the "envelope mode" is selected, the input file from playback storage 501 is ignored and a synthetic envelope is created based on the received parameter values for playback to the NIBP monitor. Blood pressure oscillations can be either synthetic or from actual patient data scaled appropriately to fit the synthesized envelope. Systolic, diastolic, MAP, and envelope amplitude may be adjusted individually. Envelope mode allows the operator to test for any blood pressure parameter settings so as to test the dynamic range of the NIBP monitor.

During data playback, data playback system 500 is started by entering the Startup file's name and the data file's name. Many of the values used to manipulate the data are output to the display screen of computer 310 if debug mode is selected. The Startup file is then analyzed and the operator is prompted to calibrate the data playback system 500 to the UUT if the calibration information is not provided in the Startup file. This information may then be used to scale the data to correspond to the calibration of the UUT as the data is received from the data file. The scaled data is stored in the memory of computer 310 and then passed on to routines that adjust the rate if needed, remove the air and cuff effects, and remove the DC offset. Also, if the Startup file parameters indicate that a noise file is to be used, the data in the noise file is scaled to the calibration of the UUT and to the requested percentage and then stored. The noise data is repeatedly summed directly into the cuff pressure channel any time oscillation complex data is being output.

After scaling and reading in all data from playback storage 501, the cuff pressure channel from UART 602 is read in. Next, the cuff pressure levels at which each of the oscillation complexes were collected are examined and the two that enclose the current cuff pressure of cuff 101 during the simulation are selected (one above and one below) for "real-time" interpolation. Real-time interpolation selects the oscillations from the data that are above and below the current pressure and scales the oscillation closest to the current cuff pressure using interpolation. This interpolation is performed while the blood pressure determination is in progress.

On the other hand, the interpolation may be done during pre-processing of the playback data. For such non-real-time interpolation, the required oscillations are generated by interpolating missing points between the existing data and storing all the oscillations, including the interpolated data, that may be needed for the blood pressure determination before it is started. Oscillations are generated for each pressure level the instrument may visit during the determination. These pre-processed oscillations are stored in a way to correspond to a given cuff pressure and are played back when the cuff pressure is at that pressure.

If amplitude variability is selected, the oscillation complex is scaled plus or minus a random percentage from zero percent to the percentage selected in the Startup file. Similarly, if rate variability is selected, the oscillation complex rate is varied by a percentage selected by the operator or by parameters in the Startup file.

If the operator wishes to introduce noise, the noise file data and the oscillation complex data are summed together and the two are converted to analog by D/A converter 502 and then added to the pressure channel of the UUT at the transducer amplifier 600 of the UUT. The cuff pressure output by transducer amplifier 600 is then read, and the above process is repeated for the next pressure level. The overall process is repeated 240 times a second. As shown in FIG. 7(c), the oscillation complex is played back repeatedly until the UUT deflates to the next pressure step.

Those skilled in the art will appreciate that the technique described herein permits more realistic simulations since the process is controlled electronically and no electromechanical diaphragms and the like are necessary. Moreover, since real patient data is used, a database of artificial waveforms need not be developed.

Those skilled in the art will also appreciate that the foregoing has set forth the presently preferred embodiment of the invention but that numerous alternative embodiments are possible without departing from the novel teachings and advantages of the invention. For example, those skilled in the art will appreciate that the techniques of the invention may be used to test blood pressure monitors in which the pressure is incremented from diastolic as described, for example, in U.S. Pat. No. 4,461,266 to Hood, Jr. et al. Also, those skilled in the art will appreciate that the techniques of the invention may be used in continuous as well as step inflate/deflate type monitors for determining the oscillometric blood pressure. Accordingly, all such modifications are intended to be included within the scope of the appended claims.

We claim:

1. A device for use in testing an oscillometric blood pressure monitor having a pressure transducer and an inflatable and deflatable pressure cuff, comprising:

means for storing oscillometric blood pressure data collected from a patient during an actual blood pressure measurement;

means for processing the oscillometric blood pressure data stored in said storing means for output; and playback means for playing back the processed data during a test of the oscillometric blood pressure monitor and electrically summing oscillation complex data corresponding to a pressure of said pressure cuff occurring during said test from said processed data with an output of said pressure transducer at said pressure of said pressure cuff occurring during said test.

2. A device as in claim 1, wherein said storing means comprises means for digitizing oscillometric blood pressure data output by said pressure transducer during said oscillometric blood pressure measurement on said patient, means for formatting said digitized oscillometric blood pressure data into data files for storage, and a memory for storing the formatted data.

3. A device as in claim 2, wherein said processing means further creates playback files for playback from said data files, each playback file comprising monitor calibration data and sampling rate data, oscillation complex amplitude data, and at least one oscillation complex for each pressure level for which oscillation complexes are measured during the oscillometric blood pressure measurement of the patient.

4. A device as in claim 1, wherein said processing means comprises means for selectively interpolating the oscillometric blood pressure data stored in said storing means to correspond to cuff pressure levels used by said oscillometric blood pressure monitor during the test.

5. A device as in claim 4, wherein said interpolating means comprises means for interpolating and storing all oscillation complexes that may be needed during an actual blood pressure determination before the actual blood pressure determination and for reading out a particular oscillation complex during the test when the cuff pressure is at the pressure at which the particular oscillation complex was stored.

6. A device as in claim 4, wherein said interpolating means comprises means for interpolating played back oscillation complexes in real-time by selecting oscillation complexes from said oscillation complex data that are above and below the pressure of the pressure cuff occurring during the test and by scaling an oscillation complex closest to the pressure.

7. A device as in claim 1, wherein said processing means comprises means for randomly varying amplitudes of said oscillometric blood pressure data and periods of oscillation of said oscillometric blood pressure data within limits set by an operator.

8. A device as in claim 1, wherein said processing means comprises means for varying a sampling rate of said oscillometric blood pressure data within limits set by an operator.

9. A device as in claim 1, wherein said processing means comprises means for summing external noise data with oscillation complex data from said storing means prior to being electrically summed with said output of said pressure transducer during the test.

10. A device as in claim 1, wherein said processing means comprises means for rotating each block of oscillation complex data in said storing means so that data at the ends of each said block is at the same amplitude level and for removing a DC pressure component prior to playback of the processed data by said playback means.

11. A device as in claim 1, wherein said playback means comprises means for digitizing the output of said pressure transducer during the test, means for converting the processed data from said processing means into an analog signal for summation with the output of said pressure transducer, and communication means for controlling data communication among said digitizing means, said converting means, and said processing means.

12. A method of testing an oscillometric blood pressure monitor having a pressure transducer and an inflatable and deflatable pressure cuff, comprising the steps of:

storing oscillometric blood pressure data collected from a patient during an actual oscillometric blood pressure measurement;

playing back the stored data during a test of the oscillometric blood pressure monitor; and during the test, electrically summing oscillation complex data corresponding to a pressure of said pressure cuff occurring during said test which is played back during said playing back step with an output of said pressure transducer at said pressure of said pressure cuff occurring during said test.

13. A method as in claim 12, wherein said storing step comprises the steps of digitizing oscillometric blood pressure data output by said pressure transducer during said oscillometric blood pressure measurement on said patient and of formatting said digitized oscillometric blood pressure data into data files for storage.

14. A method as in claim 13, wherein said formatting step comprises the step of creating playback files for playback from said data files, each playback file comprising monitor calibration data and sampling rate data, oscillation complex amplitude data, and at least one oscillation complex for each pressure level for which oscillation complexes are measured during the oscillometric blood pressure measurement of the patient.

15. A method as in claim 12, wherein said playing back step comprises the steps of interpolating and storing all oscillation complexes that may be needed during an actual blood pressure determination before the actual blood pressure determination, and reading out a particular oscillation complex during the test when the cuff pressure is at the pressure at which the particular oscillation complex was stored.

16. A method as in claim 12, wherein said playing back step comprises the steps of digitizing the output of said pressure transducer during the test, determining the cuff pressure level at which oscillation complexes are being searched for by said oscillometric blood pressure monitor during the test, selecting the oscillation complex stored in said storing step which was collected at a pressure level that is closest to the cuff pressure level occurring during said test and digitizing the oscillation complex selected in said selecting step.

17. A method as in claim 16, wherein said playing back step comprises the further step of selectively interpolating the oscillometric blood pressure data stored in said storing step for cuff pressure levels on either side of the cuff pressure level occurring during said test in order to determine the oscillation complex amplitude for the cuff pressure level occurring during said test.

18. A method as in claim 12, wherein said playing back step comprises the further step of randomly varying amplitudes of said oscillometric blood pressure data and periods of oscillations of said oscillometric blood pressure data within limits set by an operator.

19. A method as in claim 12, wherein said playing back step comprises the further step of varying a sampling rate of said oscillometric blood pressure data within limits set by an operator.

20. A method as in claim 12, wherein said playing back step comprises the further step of summing external noise data with oscillation complex data prior to said summing step.

21. A method as in claim 12, wherein said playing back step comprises the further steps of rotating each block of oscillation complex data so that data at the ends of each said block is at the same amplitude level and removing a DC pressure component prior to summing with the output of said pressure transducer in said summing step.

22. A device for use in testing an oscillometric blood pressure monitor having a pressure transducer and an inflatable and deflatable pressure cuff, comprising:

means for storing oscillometric blood pressure patient data collected from a patient during an actual blood pressure measurement;

means for creating a synthetic envelope including means for scaling real or synthetic oscillation complexes to fit said synthetic envelope; and playback means for playing back the synthetic envelope data during a test of the oscillometric blood pressure monitor and electrically summing the synthetic envelope data corresponding to a pressure of said pressure cuff occurring during said test with an output of said pressure transducer at said pressure of said pressure cuff occurring during said test.

23. A device for use in testing an oscillometric blood pressure monitor having a pressure transducer and an inflatable and deflatable pressure cuff, comprising:

a playback memory which stores digitized oscillometric blood pressure data collected from a patient during an actual oscillometric blood pressure measurement;

a processor which processes the oscillometric blood pressure data stored in said playback memory for output;

a digital to analog converter which converts to an analog pressure signal oscillation complex data in the oscillometric blood pressure data output by said processor; and an analog summer which electrically sums the analog pressure signal with an output of the pressure transducer in accordance with a pressure of said pressure cuff occurring during a test of an oscillometric blood pressure monitor.

24. A device as in claim 23, further comprising an analog to digital converter which digitizes oscillometric blood pressure data output by said pressure transducer during said oscillometric blood pressure measurement on said patient, and said processor is programmed to format said digitized oscillometric blood pressure data into data files for storage in said playback memory.

25. A device as in claim 24, wherein said processor is further programmed to create playback files for playback from said data files, each playback file comprising monitor calibration data and sampling rate data, oscillation complex amplitude data, and at least one oscillation complex for each pressure level for which oscillation complexes are measured during the oscillometric blood pressure measurement of the patient.

26. A device as in claim 23, wherein said processor is programmed to selectively interpolate the oscillometric blood pressure data stored in said playback memory to correspond to cuff pressure levels used by said oscillometric blood pressure monitor during the test.

27. A device as in claim 26, wherein said processor is programmed to interpolate and store all oscillation complexes that may be needed during an actual blood pressure determination before the actual blood pressure determination and to read out a particular oscillation complex during the test when the cuff pressure is at the pressure at which the particular oscillation complex was stored.

28. A device as in claim 26, wherein said processor is programmed to interpolate played back oscillation complexes in real-time by selecting oscillation complexes from said oscillation complex data that are above and below the pressure of the pressure cuff occurring during the test and by scaling an oscillation complex closest to the pressure occurring during said test.

29. A device as in claim 23, wherein said processor is programmed to randomly vary amplitudes of said oscillometric blood pressure data and periods of oscillation of said oscillometric blood pressure data within limits set by an operator.

30. A device as in claim 23, wherein said processor is programmed to vary a sampling rate of said oscillometric blood pressure data within limits set by an operator.

31. A device as in claim 23, wherein said processor is programmed to sum external noise data with oscillation complex data from said playback memory prior to being electrically summed with said output of said pressure transducer by said analog summer during the test.

32. A device as in claim 23, wherein said processor is programmed to rotate each block of oscillation complex data in said playback memory so that data at ends of each said block are at the same amplitude level and to remove a DC pressure component prior to outputting the processed oscillation complex data to the digital to analog converter.

33. A device as in claim 24, further comprising a transceiver which controls data communication among said analog to digital converter, said digital to analog converter, said playback memory, and said processor.

* * * * *